(12) United States Patent
Kuzuhara et al.

(10) Patent No.: US 12,189,103 B2
(45) Date of Patent: Jan. 7, 2025

(54) OPTICAL SYSTEM (71) Applicant: Panasonic Intellectual Property Management Co., Ltd., Osaka (JP)

(72) Inventors: Satoshi Kuzuhara, Osaka (JP); Tsuneo Uchida, Chiba (JP)

(73) Assignee: INTELLECTUAL PROPERTY MANAGEMENT CO., LTD., Osaka (JP)

(*) Notice: Subject to any disclaimer, the term of this patent is extended or adjusted under 35 U.S.C. 154(b) by 667 days.

(21) Appl. No.: 17/405,723

(22) Filed: Aug. 18, 2021

(65) Prior Publication Data

US 2021/0373304 A1 Dec. 2, 2021

Related U.S. Application Data (63) Continuation of application No. PCT/JP2020/016173, filed on Apr. 10, 2020.

(30) Foreign Application Priority Data

Apr. 26, 2019 (JP) ................... 2019-086438

(51) Int. Cl.
G02B 17/08 (2006.01)
A61B 3/10 (2006.01)
G02B 26/10 (2006.01)

(52) U.S. Cl.
CPC ............ G02B 17/08 (2013.01); G02B 26/10 (2013.01); *A61B 3/1015* (2013.01); *A61B 3/1025* (2013.01)

(58) Field of Classification Search
CPC ............. G02B 17/08; G02B 17/0816; G02B 17/086; G02B 26/10; G02B 26/101; G02B 3/06; A61B 3/1015; A61B 3/1025
(Continued)

(56) References Cited

U.S. PATENT DOCUMENTS 7,054,075 B2 * 5/2006 Nishioka ................. G02B 1/06
359/290
7,515,194 B2 * 4/2009 Nagata ................. G02B 13/007
359/833

(Continued)

FOREIGN PATENT DOCUMENTS

JP 2007-094121 4/2007
JP 2018-108400 7/2018

OTHER PUBLICATIONS

Office Action issued Jan. 9, 2024 in corresponding Japanese Patent Application No. 2021-515987, with English language translation.
(Continued)

*Primary Examiner* — George G. King
*Assistant Examiner* — Anna Smith
(74) *Attorney, Agent, or Firm* — Wenderoth, Lind & Ponack, L.L.P.

(57) ABSTRACT

The present disclosure provides an optical system that includes a prism having an incident surface, an exit surface, and one or more reflecting surfaces. The optical system includes a first scanning element configured to scan in a first direction a light that enters and reflect the light in a direction of the incident surface of the prism, and a second scanning element configured to scan in a second direction the light that exits from the exit surface of the prism, the second direction being orthogonal to the first direction. The incident surface of the prism has a convex shape with respect to the first scanning element.

26 Claims, 10 Drawing Sheets

(58) Field of Classification Search
USPC .......................................................... 359/720
See application file for complete search history.

(56) References Cited

U.S. PATENT DOCUMENTS

2002/0101666 A1\* 8/2002 Togino .................. G02B 15/04
   359/720
2015/0216408 A1   8/2015 Brown et al.
2024/0264415 A1\* 8/2024 Saiga ................ G02B 17/0816

OTHER PUBLICATIONS

Office Action issued Sep. 5, 2023 in corresponding Chinese Patent Application No. 202080007614.6, with English language translation.
Extended European Search Report issued May 20, 2022 in corresponding European Patent Application No. 20793955.4.
Translation of the International Preliminary Report on Patentability issued Nov. 4, 2021 in corresponding International Application No. PCT/JP2020/016173.
International Search Report issued Jul. 14, 2020 in International (PCT) Application No. PCT/JP2020/016173.

\* cited by examiner

OPTICAL SYSTEM

CROSS-REFERENCE TO RELATED APPLICATIONS

This is a continuation application of International Application No. PCT/JP2020/016173, with an international filing date of Apr. 10, 2020, which claims priority of Japanese Patent Application No. 2019-086438 filed on Apr. 26, 2019, the content of which is incorporated herein by reference.

TECHNICAL FIELD

The present disclosure relates to an optical system using a prism.

BACKGROUND

JP 2018-108400 A discloses an optical system having a scanning device that scans in two directions. It is described that this optical system transmits a scanned laser using a mirror. When the laser is transmitted using the mirror, since there is a layer of air between mirrors, it is difficult to reduce the size of the optical system.

SUMMARY

When a space between mirrors is filled with medium of prism, an optical system can be downsized, but further downsizing has been required.

The present disclosure provides a downsized optical system using the prism.

An optical system according to the present disclosure includes a prism having an incident surface, an exit surface, and one or more reflecting surfaces, a first scanning element that scans an incident light in a first direction and reflects the incident light in a direction of the incident surface of the prism, and a second scanning element that scans the light exiting from the exit surface of the prism in a second direction orthogonal to the first direction. The incident surface of the prism has a convex shape with respect to the first scanning element.

An optical system according to the present disclosure includes a prism having an incident surface, an exit surface, and one or more reflecting surfaces, a first scanning element that scans an incident light in a first direction and reflects the incident light in a direction of the incident surface of the prism, and a second scanning element that scans the light exiting from the exit surface of the prism in a second direction orthogonal to the first direction. The exit surface of the prism has a convex shape with respect to the second scanning element.

An optical system according to the present disclosure includes a prism having an incident surface, an exit surface, and one or more reflecting surfaces, a first scanning element that scans an incident light in a first direction and reflects the incident light in a direction of the incident surface of the prism, and a second scanning element that scans the light exiting from the exit surface of the prism in a second direction orthogonal to the first direction. The prism has a first reflecting surface that reflects the light emitted from the incident surface, and a second reflecting surface that reflects a light reflected by the first reflecting surface. An optical path length L1 from the incident surface to the first reflecting surface and an optical path length L2 from the first reflecting surface to the second reflecting surface satisfy L1<L2.

An optical system of the present disclosure can provide a downsized optical system using a prism.

DETAILED DESCRIPTION

Hereinafter, embodiments will be described in detail with reference to the drawings as appropriate. However, unnecessarily detailed description may be omitted. For example, a detailed description of a well-known matter and a repeated description of substantially the same configuration may be omitted. This is to avoid unnecessary redundancy in the following description and to facilitate understanding of those skilled in the art.

Note that the inventor (s) provides the accompanying drawings and the following description in order for those skilled in the art to fully understand the present disclosure, and does not intend to limit the subject matter described in the claims by the accompanying drawings and the following description.

First Embodiment

The first embodiment will be described below with reference to FIGS. 1 to 9. In the present embodiment, as illustrated in FIG. 2, for example, an X direction is a long diameter direction of a pupil diameter 11a of a laser light R emitted from a laser element 11, and a Y direction is a short diameter direction of the pupil diameter 11a of the laser light R emitted from the laser element 11. The X direction and the Y direction are orthogonal to each other, and a direction orthogonal to an XY plane is a Z direction.

1-1. Configuration

Figure 1:
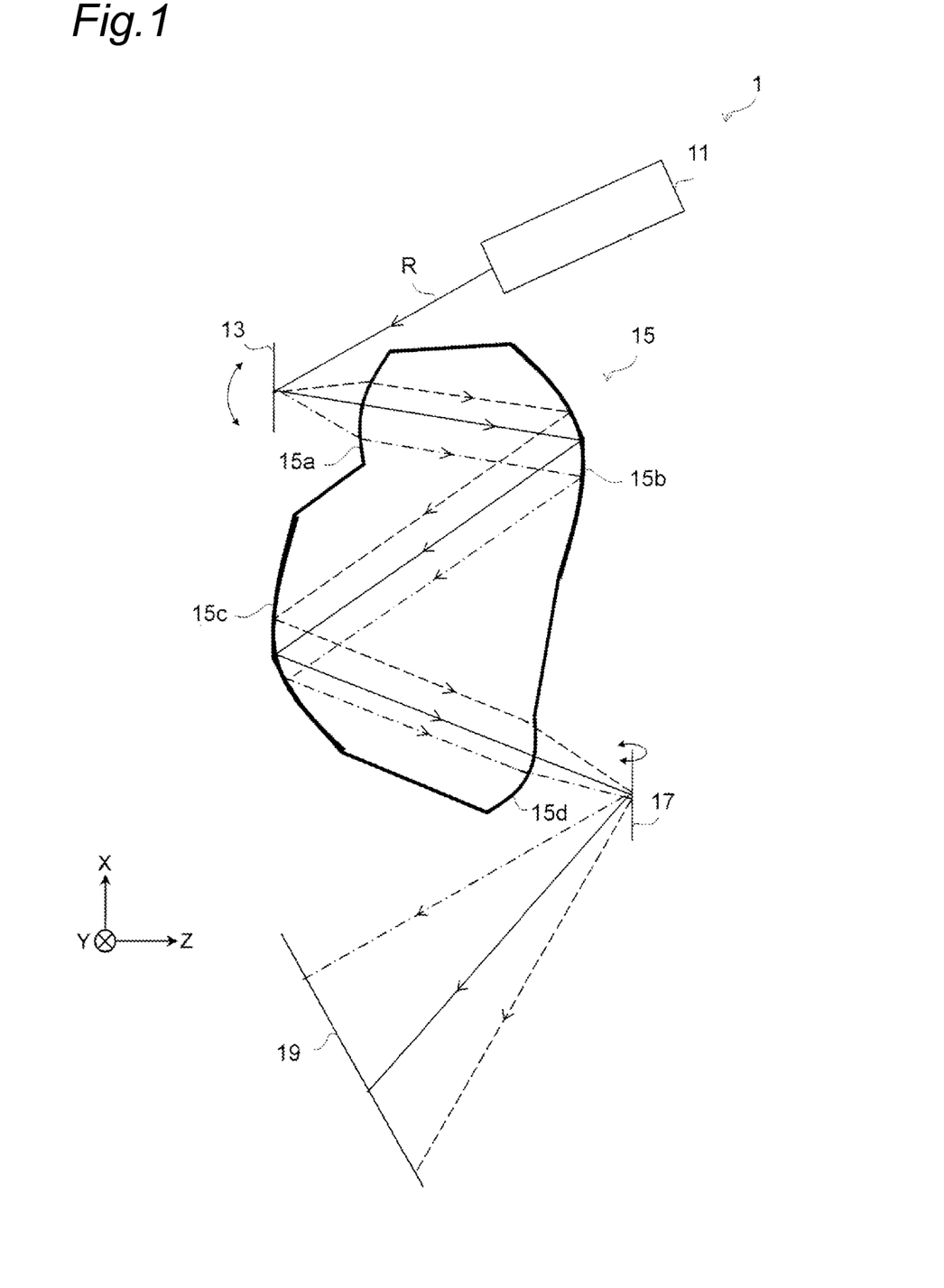
FIG. 1 is a cross-sectional view illustrating a configuration of an optical system according to a first embodiment.
Figure 2:
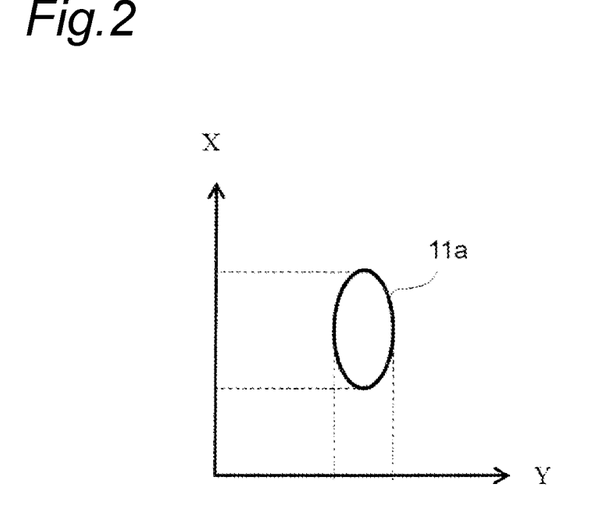
FIG. 2 is a diagram illustrating a pupil diameter of a laser light immediately after irradiation from a laser element in the first embodiment.

FIG. 1 is a cross-sectional view illustrating a configuration of an optical system 1 according to the present disclosure. The optical system 1 includes a laser element 11, a first scanning element 13, a prism 15, and a second scanning element 17.

The laser element 11 is, for example, a semiconductor laser. The laser light R emitted from the laser element 11 is a parallel light having different pupil diameters in the X direction and the Y direction. For example, as illustrated in FIG. 2, the pupil diameter 11a of a laser light R immediately after irradiation from the laser element 11 has an elliptical shape extending in the X direction. The laser light R emitted from the laser element 11 is scanned in the X direction by the first scanning element 13 and is incident on an incident surface 15a of the prism 15. The laser light R has a plurality of wavelengths (wavelength regions) so as to have, for example, colors of red (R), green (G), and blue (B). The laser element 11 may emit one light flux in which R, G, and B lights are mixed as the laser light R, or may sequentially emit the laser light R of a light flux of each color.

As illustrated in FIG. 1, the first scanning element 13 scans the incident laser light R in the X direction as the first direction. The first scanning element 13 is, for example, a mirror that is rotationally driven by piezoelectric driving in the Y direction as a rotation axis. The first scanning element 13 is, for example, a scanner in a vertical direction. As a result, the parallel light is diffused in the X direction.

The prism 15 has the incident surface 15a and an exit surface 15d. The prism 15 further has one or more reflecting surfaces in an optical path from the incident surface 15a to the exit surface 15d. In the present embodiment, for example, the prism 15 has a first reflecting surface 15b and a second reflecting surface 15c. The prism 15 is made of, for example, resin or glass.

The incident surface 15a faces the first scanning element 13, and the laser light R scanned in the X direction by the first scanning element 13 is incident on the prism 15 through the incident surface 15a. The incident surface 15a and the first reflecting surface 15b face each other, and the laser light R incident from the incident surface 15a is reflected by the first reflecting surface 15b into the prism 15.

Figure 3:
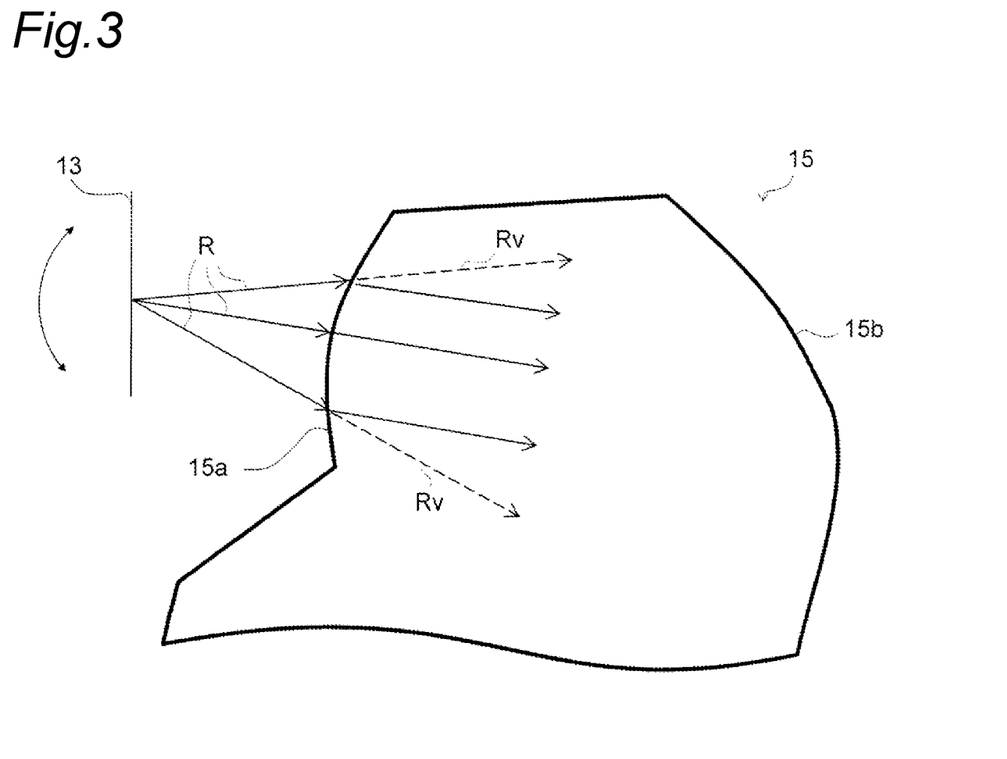
FIG. 3 is an enlarged cross-sectional view of an incident surface of a prism.

As illustrated in FIG. 3, the incident surface 15a has a convex shape with respect to the first scanning element 13. The incident surface 15a has a curved surface shape having a curvature along the X direction in which the first scanning element 13 scans, and protrudes outward from the prism 15. FIG. 3 illustrates, as a comparative example, a traveling direction Rv of the laser light R in a case where the incident surface 15a does not have the convex shape. By making the shape of the incident surface 15a the convex shape, the laser light R incident on the incident surface 15a can be refracted inward. As described above, the laser light R scanned in the X direction can travel in the prism in a state that spreading of the laser light R is suppressed, for example, as a light in which the center rays of the scanned laser light are parallel to each other, so that the prism 15 can be downsized.

The incident surface 15a may be a rotationally asymmetric surface having a convex shape with respect to the scanning direction of the first scanning element 13.

The incident surface 15a may have a smaller refractive power in the non-scanning direction than in the scanning direction of the first scanning element 13. As a result, chromatic aberration in a non-scanning direction that occurs on the incident surface 15a can be suppressed.

After the laser light R reflected by the first reflecting surface 15b forms an intermediate image, the pupil diameter of the laser light R is enlarged again and reflected again into the prism 15 by the second reflecting surface 15c. The laser light R reflected by the second reflecting surface 15c exits from the exit surface 15d to the outside of the prism 15.

The first reflecting surface 15b and the second reflecting surface 15c have different curvatures in the X direction as the first direction and the Y direction as a second direction, respectively. Therefore, the first reflecting surface 15b and the second reflecting surface 15c have a free-form surface shape.

Still more, each of the first reflecting surface 15b and the second reflecting surface 15c may be eccentric to the incident light. This makes it possible to separate the optical path of the incident light without using an optical element such as a beam splitter. Further, each of the first reflecting surface 15b and the second reflecting surface 15c has a convex shape with respect to the incident light.

The exit surface 15d of the prism 15 may also have the same configuration as the incident surface 15a. The exit surface 15d may have the convex shape with respect to the second scanning element 17. As a result, the light traveling in the prism 15 in a state that spreading of the laser light R scanned in the X direction is suppressed can be condensed on the second scanning element 17, so that the prism 15 can be downsized. For example, the exit surface 15d has a curvature along the X direction in which the first scanning element 13 scans, and protrudes outward from the prism 15. Note that the curvature in the X direction of the incident surface 15a and the exit surface 15d may have symmetry. In addition, the exit surface 15d may have a curvature along the Y direction in which the second scanning element 17 scans, and protrude outward from the prism 15. The exit surface 15d may have a rotationally asymmetric surface having the convex shape with respect to the Y direction in which the second scanning element 17 scans.

Further, the exit surface 15d may have a smaller refractive power in the non-scanning direction than in the scanning direction of the second scanning element 17.

The second scanning element 17 scans the laser light R exiting from the exit surface 15d of the prism 15 in the Y direction and projects the laser light R onto the projection surface 19. The second scanning element 17 is, for example, a mirror that is rotationally driven by piezoelectric driving in the X direction as a rotation axis. The second scanning element 17 is, for example, a horizontal scanner. In addition, the second scanning element 17 scans in synchronization with the first scanning element 13, so that a two-dimensional image can be projected on the projection surface 19.

In the optical system 1 according to the present embodiment, the first scanning element 13, the incident surface 15a of the prism 15, the first reflecting surface 15b of the prism 15, the second reflecting surface 15c of the prism 15, the exit surface 15d of the prism 15, and the second scanning element 17 are arranged in order of the optical path from the laser element 11. Therefore, the prism 15 is disposed in the optical path from first scanning element 13 to second scanning element 17.

Figure 4:
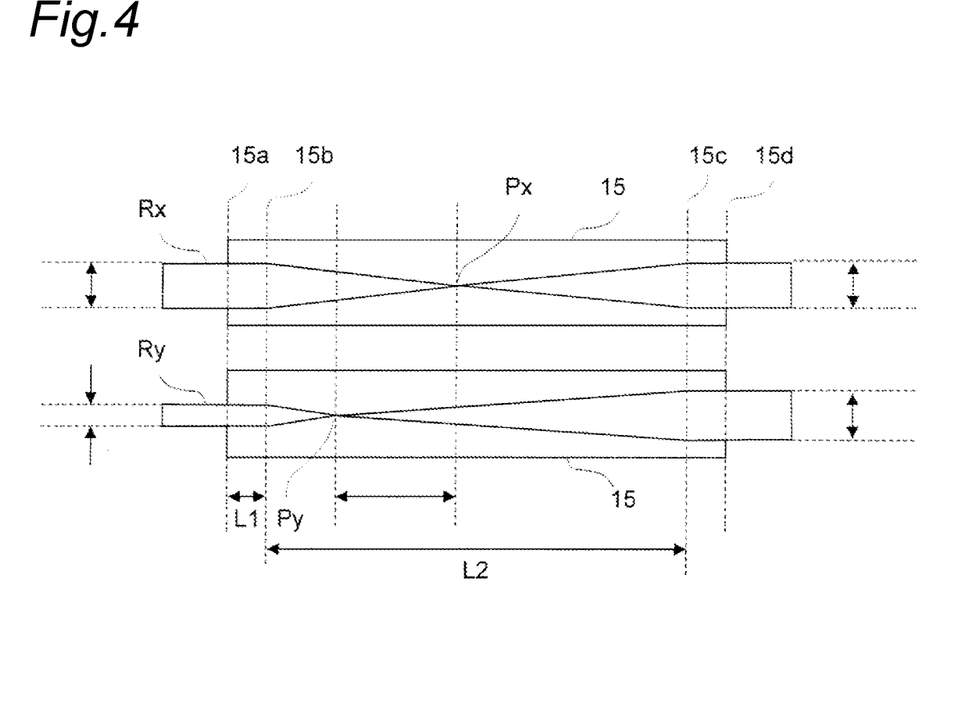
FIG. 4 is a diagram illustrating intermediate imaging positions of an X component and a Y component of the laser light.

As illustrated in FIG. 4, the optical system 1 has an intermediate imaging position Px in the X direction of a light flux of the laser light R between the first reflecting surface 15b in the prism 15 and the second reflecting surface 15c in the prism 15. In other words, the laser light R forms the intermediate image by the first reflecting surface 15b.

Still more, since focal lengths of Rx that is a component of the laser light R in the X direction, and Ry that is a component of the laser light R in the Y direction are also different, the intermediate imaging position Px of the X component Rx and the intermediate imaging position Py of the Y component Ry of the laser light R are different. Further, since focal lengths of the X component Rx and the Y component Ry are different from each other, magnification ratios at the time of emission from the exit surface 15d of the prism 15 are also different from each other. In other words, the optical system 1 has different optical magnifications in the X direction and the Y direction. For example, in the present embodiment, since the focal length in the Y direction is longer than that in the X direction, the optical magnification in the Y direction is larger than that in the X direction.

Figure 5:
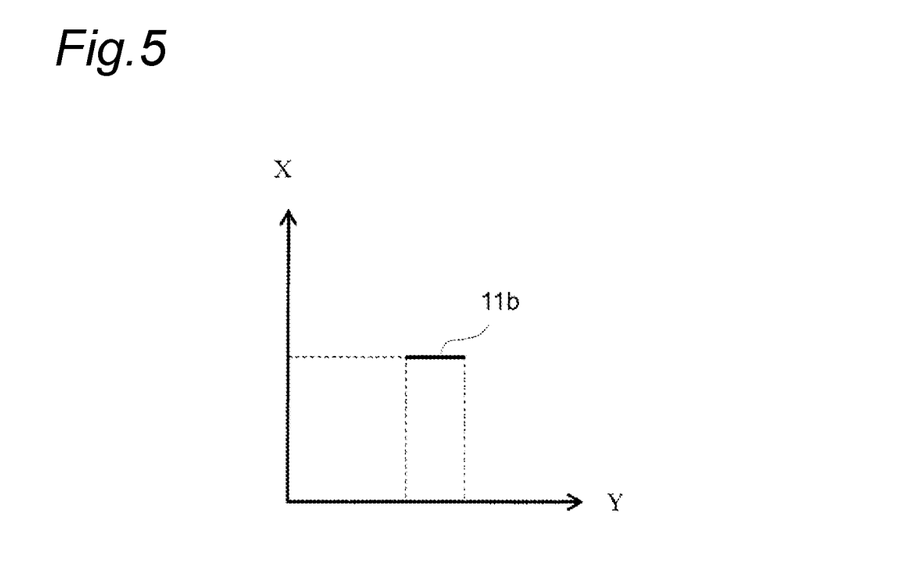
FIG. 5 is a diagram illustrating a pupil diameter of the laser light at an intermediate imaging position (Px).

The intermediate imaging position Px of the light flux of the laser light R in the X direction does not intersect at the same position with the light flux of the laser light R in the Y direction orthogonal to the X direction. In other words, the intermediate imaging position Px of the X component Rx of the laser light R is not located at the same position as the intermediate imaging position Py of the Y component Ry of the laser light R. As a result, as illustrated in FIG. 5, a pupil diameter 11b of the laser light R at the intermediate imaging position Px has a linear shape extending in the Y direction. As a result, it is possible to prevent loss of the pupil diameter 11b of the laser light R when dust or scratch exists at the intermediate imaging position Px.

Figure 6:
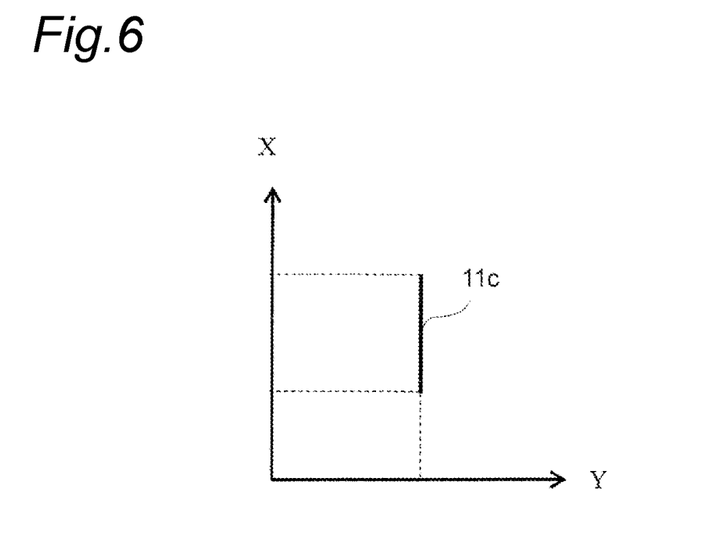
FIG. 6 is a diagram illustrating a pupil diameter of the laser light at an intermediate imaging position (Py).
Figure 7:
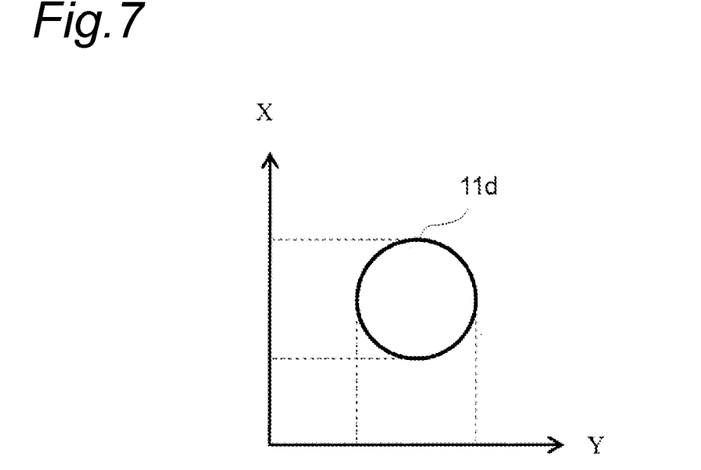
FIG. 7 is a diagram illustrating a pupil diameter of the laser light exiting from the prism.

Further, as illustrated in FIG. 6, at the intermediate imaging position Py of the Y component Ry of the laser light R, a pupil diameter 11c of the laser light R exists before the X component Rx of the laser light R forms an image. In this manner, the pupil diameter 11c of the laser light R at the intermediate imaging position Py also has a linear shape extending in the X direction. Since an optical magnification of the optical system 1 is larger in the Y direction than in the X direction, a pupil diameter 11d of the laser light R exiting from the exit surface 15d is formed in a circular shape as illustrated in FIG. 7.

A relationship between a first exit pupil diameter φx1 in the X direction and a second exit pupil diameter φy1 in the Y direction of the light emitted from the laser element 11, and a first projection pupil diameter φx2 in the X direction and a second projection pupil diameter φy2 in the Y direction of the light passing through the exit surface 15d of the prism 15 and reaching the projection surface 19 is as follows:

$0.1 < (\varphi x1 \times \varphi y1)/(\varphi x2 \times \varphi y2) < 0.8$. By satisfying this relationship, spot sizes at the intermediate imaging positions Px and Py increase, and an influence of dust or scratch inside the prism 15 can be effectively reduced.

Figure 8:
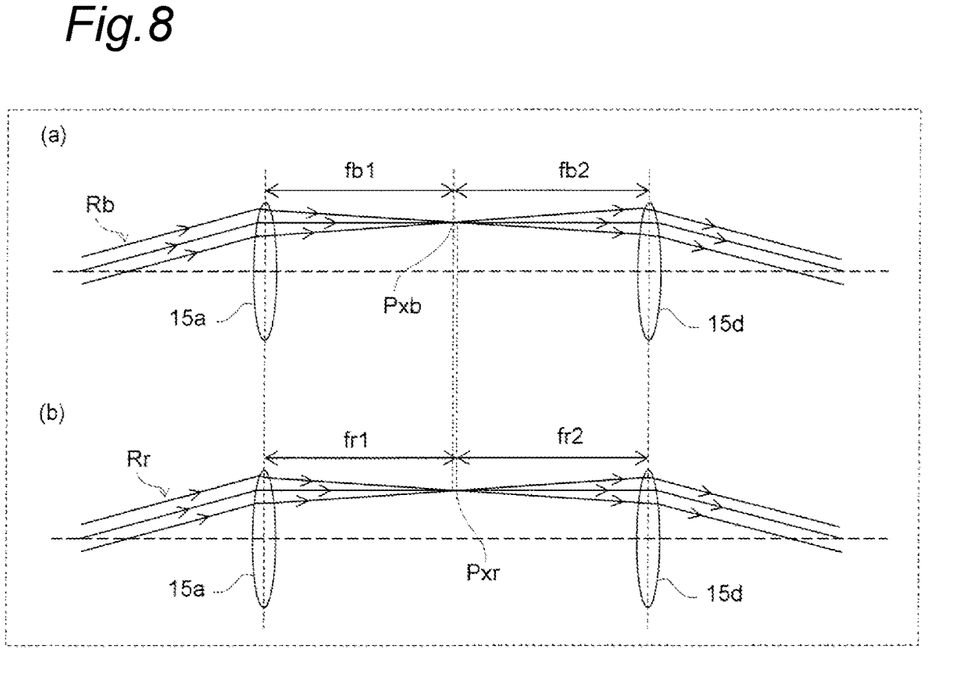
FIG. 8 is a diagram illustrating an intermediate imaging position of each of red and blue laser lights.

Next, with reference to FIG. 8, it will be described that the optical system 1 of the first embodiment reduces chromatic aberration that occurs by the incident surface 15a of the prism 15. FIG. 8(a) is a diagram illustrating an intermediate imaging position Pxb of a blue laser light Rb, and FIG. 8(b) is a diagram illustrating an intermediate imaging position Pxr of a red laser light Rr. Note that, in FIGS. 8(a) and 8(b), the incident surface 15a and the exit surface 15d are illustrated as lenses for simple description.

When the lights of R, G, and B having different wavelengths are made incident from the incident surface 15a having the convex shape, a refractive power varies depending on the wavelength, so that the focal lengths of the lights of the respective wavelengths are different. Hereinafter, the blue laser light Rb and the red laser light Rr having a large wavelength difference will be described. The blue laser light Rb made incident from the incident surface 15a forms the intermediate imaging position Pxb at a position of a focal length fb1. A distance between the intermediate imaging position Pxb and the exit surface 15d is a focal length fb2. In addition, the red laser light Rr made incident from the incident surface 15a forms the intermediate imaging position Pxr at a position of a focal length fr1. A distance between the intermediate imaging position Pxr and the exit surface 15d is a focal length fr2.

The focal lengths fb1 and fr1 determine angles of the light after passing through the incident surface 15a, respectively. Since the refractive power becomes stronger as the wavelength of the light is shorter, the focal length fb1 of the blue laser light Rb is shorter than the focal length fr1 of the red laser light Ra. As a result, chromatic aberration of magnification is likely to occur due to a difference in color. Therefore, the intermediate imaging position Pxb of the blue laser light Rb is located closer to the incident surface 15a than the red intermediate imaging position Pxr.

In the case of an optical system that does not form an intermediate imaging position in the optical path between the first scanning element and the second scanning element, a difference between the focal lengths fb1 and fr1 results in a shift in an angle of incidence on the projection surface 19. As a result, chromatic aberration of magnification occurs. Therefore, the larger the difference between the focal lengths fb1 and fr1, the larger the chromatic aberration of magnification. However, when the intermediate imaging positions Pxb and Pxr are formed in the optical path between the first scanning element 13 and the second scanning element 17 as in the first embodiment, the chromatic aberration of magnification that occurs on the exit surface 15d acts to correct the chromatic aberration of magnification that occurs on the incident surface 15a. An angle of view on the exit side is determined by a ratio between the focal lengths fb1 and fr1 and the focal lengths fb2 and fr2.

Since the incident surface 15a and the exit surface 15d are the same prism and the same material, a difference between fb1/fb2 and fr1/fr2, which is a difference in the ratio of the focal lengths, is smaller than the difference between fb1 and fr1. As a result, the chromatic aberration of magnification of the light incident on the projection surface 19 is reduced, compared with the optical system that does not form the intermediate image in the optical path between the first scanning element and the second scanning element. When the focal length from the incident surface 15a to the intermediate imaging position is equal to the focal length from the intermediate imaging position to the exit surface 15d (fb1=fb2, fr1=fr2), the chromatic aberration of magnification is reduced to zero.

Figure 9:
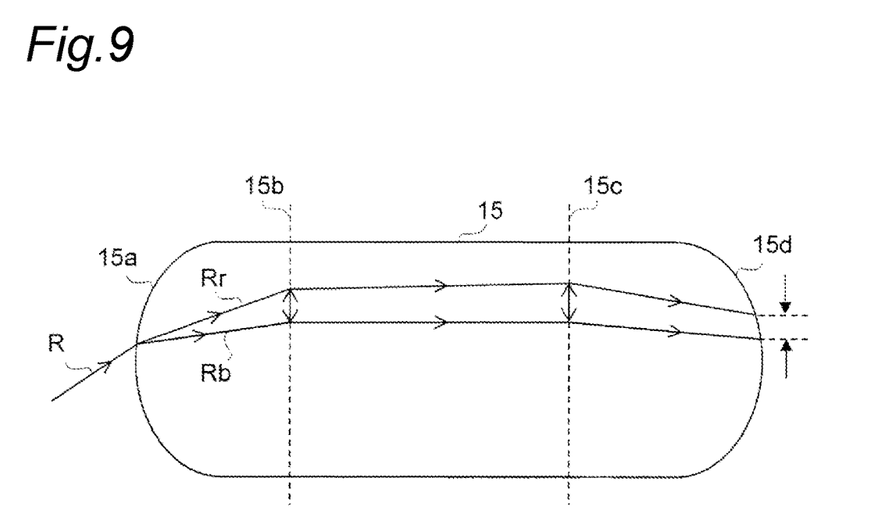
FIG. 9 is a diagram illustrating refraction of each of the red and blue laser lights on the incident surface of the prism.

In addition, as illustrated in FIG. 9, by using the reflecting surfaces 15b and 15c in which chromatic aberration does not occur inside the prism 15, it is possible to correct an influence of other aberrations, such as axial chromatic aberration and field curvature aberration, caused by the difference in refractive power on the incident surface 15a. The laser light R made incident from the incident surface 15a is dispersed into a light of each color due to a difference in refractive power. For example, the blue laser light Rb is refracted more inward than the red laser light Rr. Therefore, the blue laser light Rb and the red laser light Rr are reflected at different positions on reflecting surfaces 15b, 15c. Since the red laser light Rr is reflected at a higher position on the reflecting surfaces 15b and 15c, the red laser light Rr has a larger bending action than the blue laser light Rb. As a result, an angle difference generated on the incident surface 15a can be reduced, and an angle difference of each color of light exiting from the exit surface 15d can be suppressed.

Figure 10:
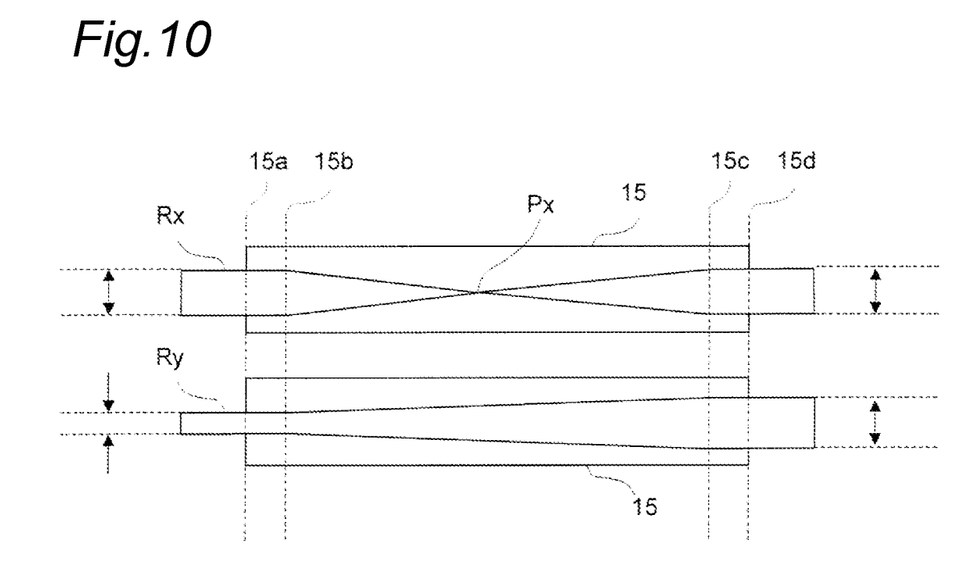
FIG. 10 is a diagram illustrating an intermediate imaging position of the X component of the laser light.

In the present embodiment, the optical system 1 has the intermediate imaging position Py in the Y direction. However, as illustrated in FIG. 10, the optical system 1 may be configured not to have an intermediate imaging action in the Y direction and there is no intermediate imaging position Py. In this case, a curvature of the first reflecting surface 15b may be designed such that the Y component Ry of the laser light R reflected by the first reflecting surface 15b gradually increases.

The present embodiment is configured with a combination of the first scanning element 13 that is a scanner in the vertical direction and the second scanning element 17 that is a scanner in the horizontal direction. However the present embodiment may be configured with the first scanning element 13 that is a scanner in the horizontal direction and the second scanning element 17 that is a scanner in the vertical direction. As a result, the size of the incident surface 15a can be reduced.

In the present embodiment, the prism 15 has two reflecting surfaces that are the first reflecting surface 15b and the second reflecting surface 15c. However, the prism 15 may have only the first reflecting surface 15b or at least two or more reflecting surfaces.

In the present embodiment, the optical system 1 includes the laser element 11, the first scanning element 13, the prism 15, and the second scanning element 17, but an optical element having refractive power may be added.

In the present embodiment, the intermediate imaging position Px is formed in the prism 15, but an optical element having a refractive power may be added in an optical path from the laser element 11 to the prism 15 to form the intermediate imaging position Px outside the prism 15.

As illustrated in FIG. 4, an optical path length L1 from the incident surface 15a to the first reflecting surface 15b and an optical path length L2 from the first reflecting surface 15b to the second reflecting surface 15c satisfy a relationship of L1<L2. According to this configuration, since the optical path length from the first reflecting surface 15b to the second reflecting surface 15c is longer than the optical path length from the incident surface 15a to the first reflecting surface 15b, as illustrated in FIG. 1, the incident surface 15a can be disposed closer to the first reflecting surface 15b side (+Z direction side) than the second reflecting surface 15c, so that the first scanning element 13 can also be disposed closer to the first reflecting surface 15b side (+Z direction side). As a result, the size of the entire optical system 1 can be reduced.

1-2. Effects

The optical system 1 according to the first embodiment includes the prism 15 having the incident surface 15a, the exit surface 15d, and one or more reflecting surfaces 15b and 15c. In addition, the optical system 1 includes the first scanning element 13 that scans the incident light in the first direction and reflects the light in the direction of the incident surface 15a of the prism 15, and the second scanning element 17 that scans the laser light R exiting from the exit surface 15d of the prism 15 in the Y direction orthogonal to the X direction. The incident surface 15a of the prism 15 has a convex shape with respect to the first scanning element 13. With such a configuration, when the laser light R scanned in the X direction by the first scanning element 13 is incident on the incident surface 15a of the prism 15, the laser light R scanned and diffused is refracted so as to become close to parallel by the incident surface 15a. Therefore, it is possible to suppress spreading of the optical path of the laser light R traveling in the prism 15. As a result, the prism 15 can be downsized. In addition, by passing the laser light R through the prism 15, the optical path length can be shortened by the refractive index of the prism 15 to downsize the optical system 1.

The optical system 1 according to the first embodiment includes the prism 15 having the incident surface 15a, the exit surface 15d, and one or more reflecting surfaces 15b and 15c. In addition, the optical system 1 includes the first scanning element 13 that scans the incident light in the first direction and reflects the light in the direction of the incident surface 15a of the prism 15, and the second scanning element 17 that scans the laser light R exiting from the exit surface 15d of the prism 15 in the Y direction orthogonal to the X direction. The exit surface 15d of the prism 15 has the convex shape with respect to the second scanning element 17. As described above, even when only the exit surface 15d has the convex shape, the light incident on the exit surface 15d from the reflecting surface 15c of the prism 15 can converge on the second scanning element 17 while being nearly parallel. As a result, the prism 15 can be downsized. In addition, by passing the laser light R through the prism 15, the optical path length can be shortened by the index (refractive index) of the prism 15 to downsize the optical system 1.

Second Embodiment

Next, the second embodiment will be described with reference to FIG. 11.

2-1. Configuration

Figure 11:
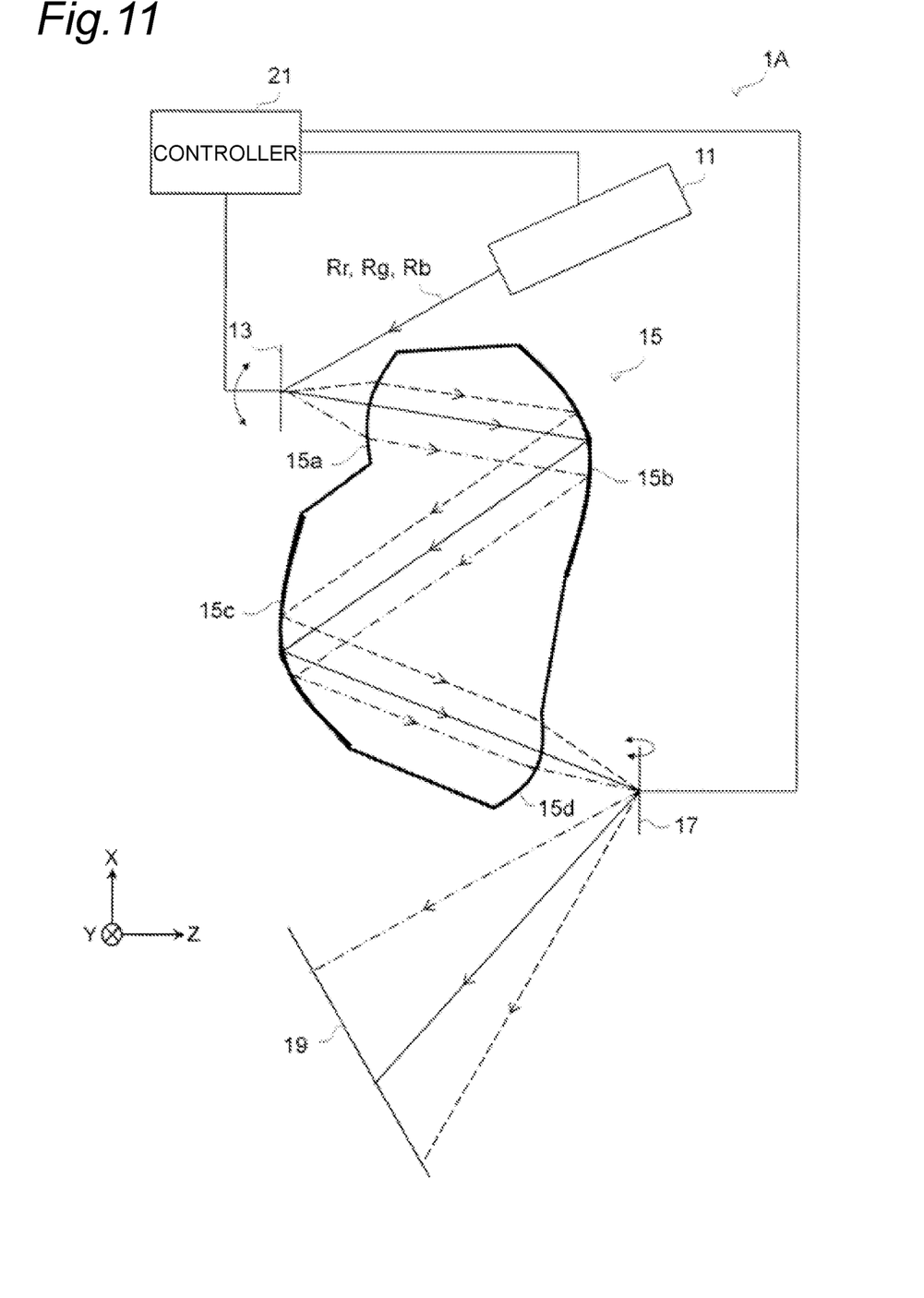
FIG. 11 is a cross-sectional view illustrating a configuration of an optical system according to a second embodiment.

FIG. 11 is a diagram illustrating a configuration of an optical system 1A according to the second embodiment. As illustrated in FIG. 11, in the optical system 1A of the present embodiment, the optical system 1 of the first embodiment further includes a controller 21 that controls the laser element 11 to shift a light emission timing of the light of each wavelength for each wavelength in synchronization with scanning by the first scanning element 13 and the second scanning element 17. The configuration other than these differences is common between the optical system 1 according to the first embodiment and the optical system 1A of the present embodiment.

For example, the laser element 11 sequentially emits laser lights Rr, Rg, and Rb of light fluxes of R, G, and B having different wavelengths at different timings. The controller 21 controls emission timings of the laser lights Rr, Rg, and Rb of respective colors in synchronization with scanning timings of the first scanning element 13 and the second scanning element 17. As a result, it is possible to further reduce deviation of an image projected on the projection surface 19 due to chromatic aberration.

Controller 21 can be implemented by a semiconductor element or the like. The controller 21 can be configured with, for example, a microcomputer, a CPU, an MPU, a GPU, a DSP, an FPGA, or an ASIC. A function of the controller 21 may be configured only by hardware, or may be realized by combining hardware and software. The controller 21 includes a storage such as a hard disk (HDD), an SSD, and a memory, and realizes a predetermined function by reading data and programs stored in the storage to perform various arithmetic processing.

2-2. Effects

Since the optical system 1A including the controller 21 controls the emission timings of the laser lights Rr, Rg, and Rb of the respective colors according to the scanning timings of the first scanning element 13 and the second scanning element 17, it is possible to correct deviation of an image projected on the projection surface 19 due to chromatic aberration.

Other Embodiments

As described above, the first and second embodiments have been described as examples of the technique disclosed in the present disclosure. However, the technique in the present disclosure is not limited thereto, and can also be applied to embodiments in which changes, replacements, additions, omissions, and the like are made. In addition, it is also possible to combine the components described in the first and second embodiments to form a new embodiment.

Figure 12:
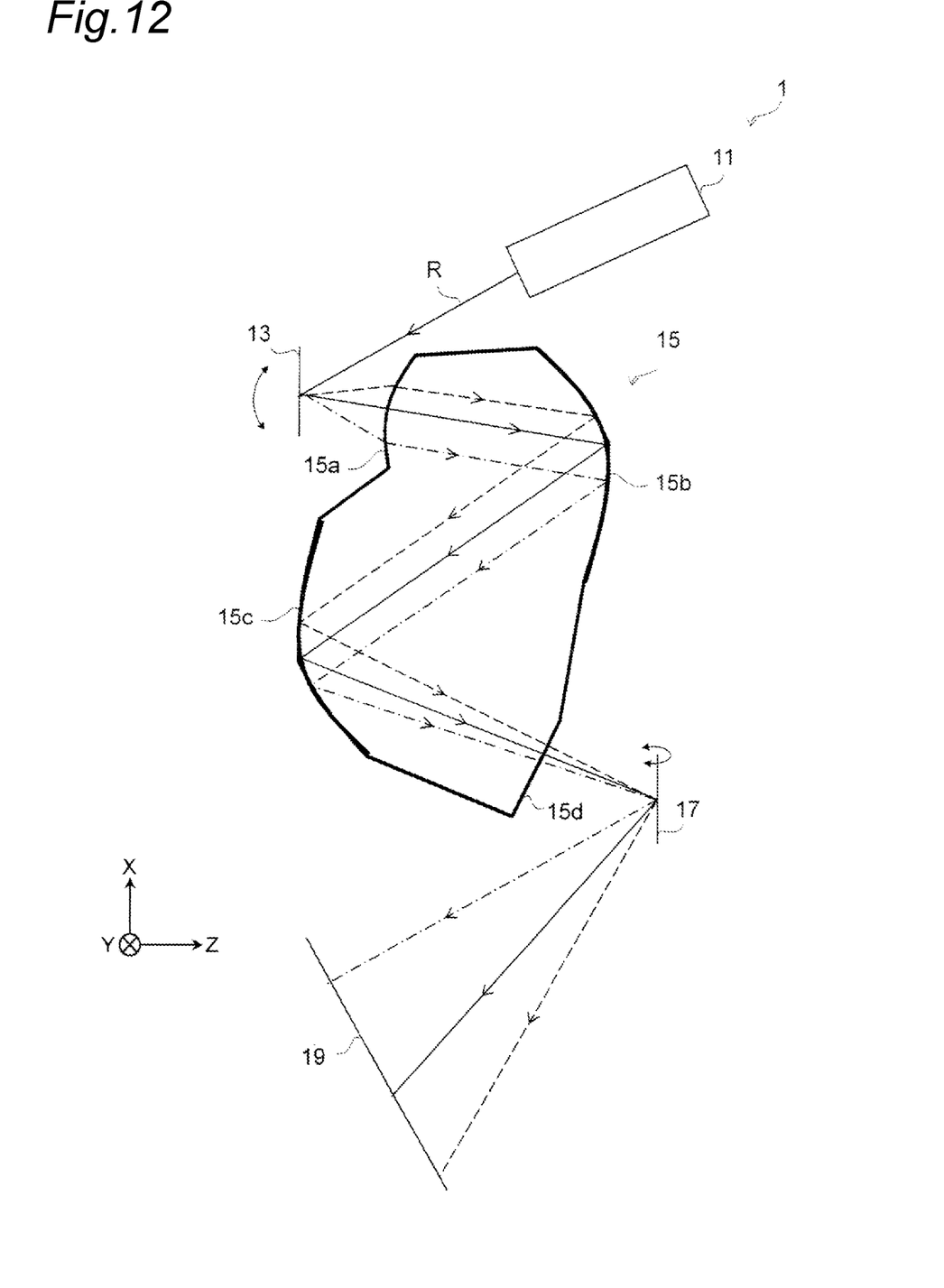
FIG. 12 is a cross-sectional view illustrating a configuration of an optical system in a modified example.

In the first and second embodiments, the exit surface 15d of the prism 15 also has the convex shape, but the present invention is not limited thereto. The exit surface 15d of the prism 15 may have a non-convex shape, for example, a flat plate shape as illustrated in FIG. 12. As described above, only the incident surface 15a of the prism 15 may have the convex shape with respect to the scanning direction of the first scanning element 13. In this case, the second reflecting surface 15c and the exit surface 15d are designed such that the light reflected by the second reflecting surface 15c passes through the exit surface 15d and is condensed on the second scanning element 17.

Figure 13A:
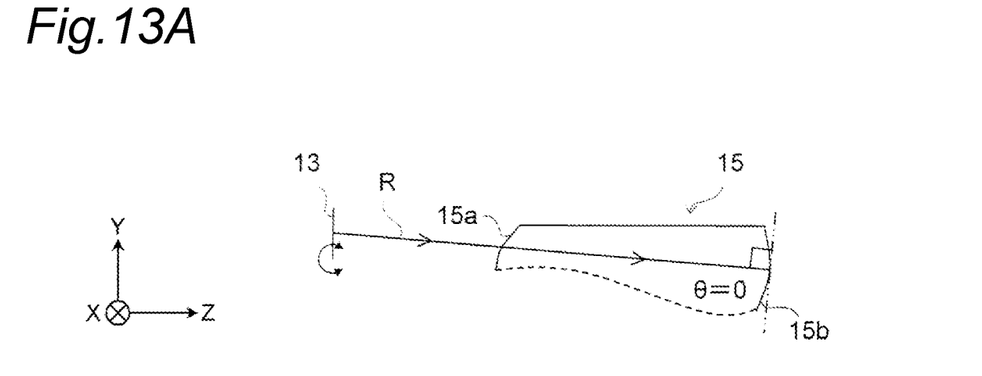
FIG. 13A is a cross-sectional view illustrating a configuration of an optical system in a comparative example.

Furthermore, the size of the prism 15 can be adjusted according to the inclination direction of the first reflecting surface 15b with respect to the incident laser light R. FIG. 13A illustrates a peripheral portion of the first reflecting surface 15b of the prism 15. As illustrated in FIG. 13A, on a plane including a scanning axis of the first scanning element 13 and the laser light R incident on the first reflecting surface 15b, when the first reflecting surface 15b is not inclined with respect to the incident laser light R, the size of the prism 15 in the Y direction decreases. For example, when an incident angle θ of the laser light R incident on the first reflecting surface 15b on a YZ plane is 0° or close to 0°, the size of the prism 15 in the Y direction decreases. On the other hand, in this case, as illustrated in FIG. 13B, on an XZ plane that is a plane orthogonal to the scanning axis of the first scanning element 13, an incident angle θ on the first reflecting surface 15 increases in the scanning direction (X direction) of the first scanning element 13, and thus, the size of the prism 15 in the X direction increases.

Figure 13B:
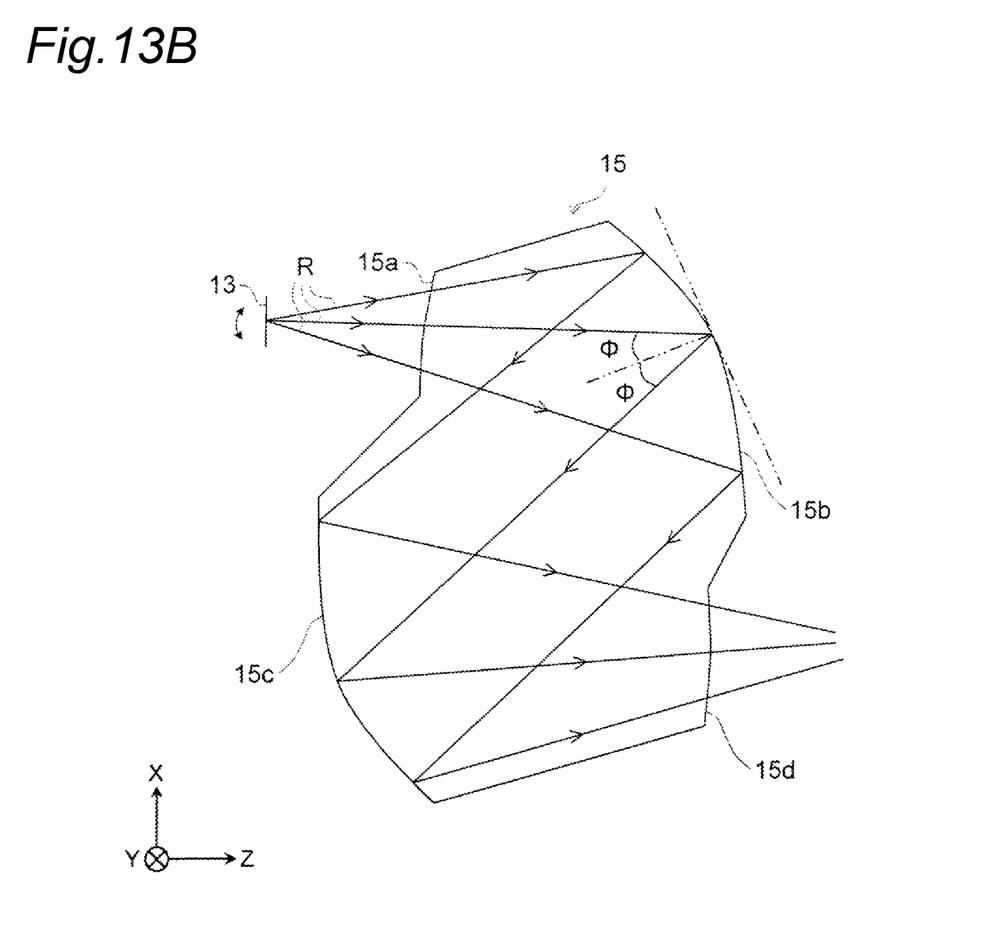
FIG. 13B is a cross-sectional view illustrating a configuration of an optical system in a comparative example.
Figure 14A:
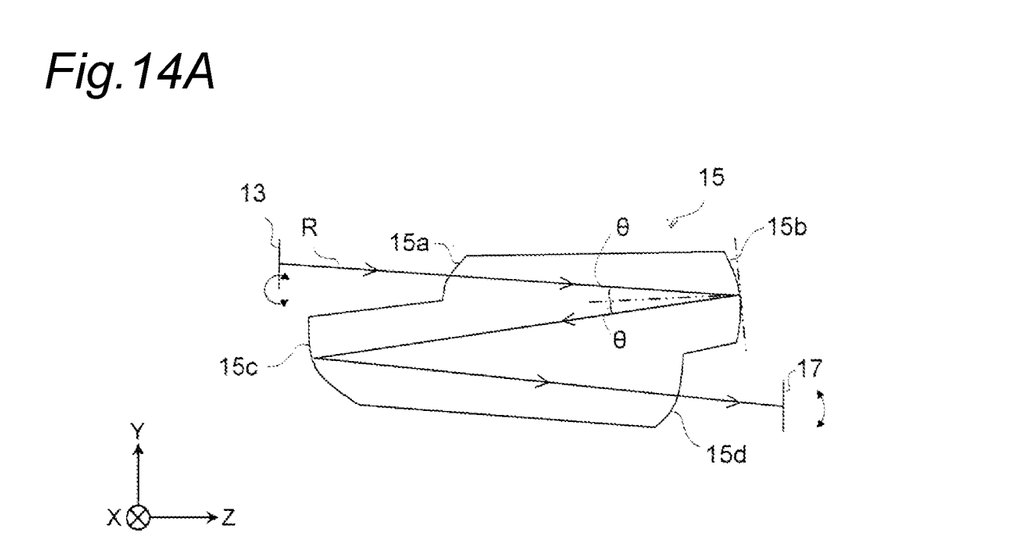
FIG. 14A is a cross-sectional view illustrating a configuration of an optical system in a modified example.
Figure 14B:
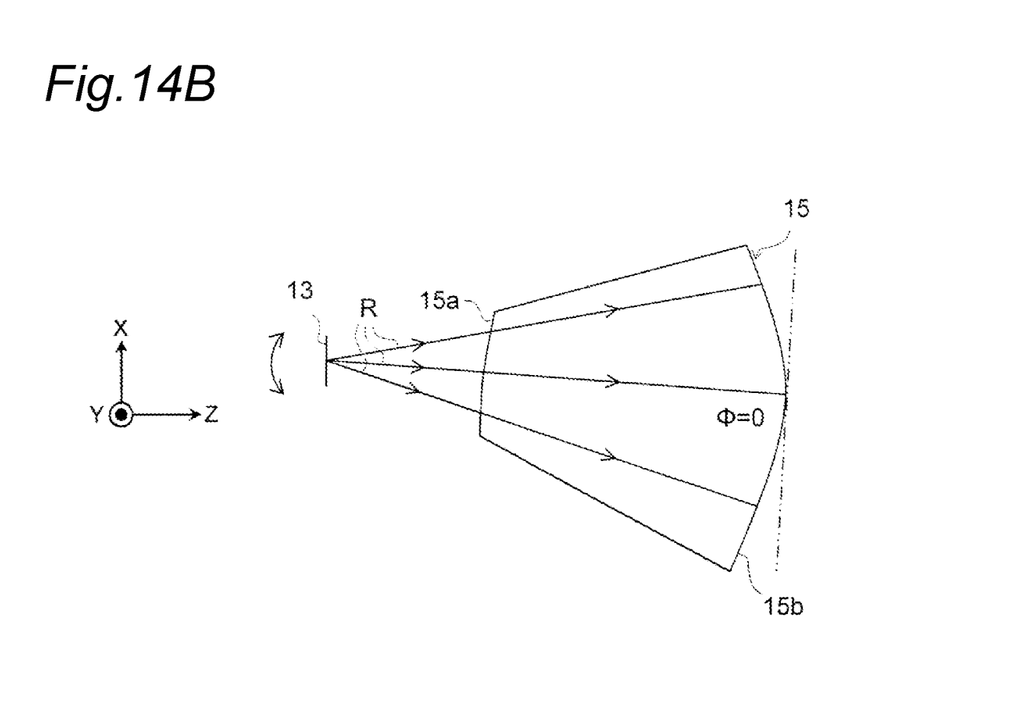
FIG. 14B is a cross-sectional view illustrating a configuration of an optical system in a modified example.

On the other hand, as illustrated in FIG. 14A, in the case where the first reflecting surface 15b is inclined with respect to the incident laser light R on a plane including the scanning axis of the first scanning element 13 and the laser light R incident on the first reflecting surface 15b, an incident angle θ can be made smaller than the incident angle θ in FIG. 13B, so that the size of the prism 15 in the Y direction can be suppressed from increasing. For example, as illustrated in FIG. 14A, when the first reflecting surface 15b is inclined with respect to the incident laser light R on the YZ plane, that is, when the laser light R is reflected at the incident angle θ with respect to the first reflecting surface 15 on the YZ plane, an increase in the size of the prism 15 in the Y direction can be suppressed. Furthermore, as illustrated in FIG. 14B, the incident angle T on the first reflecting surface 15 in the scanning direction (X direction) of the first scanning element 13 can be set to 0° on the XZ plane to reduce the size in the X direction.

In this manner, the first reflecting surface 15b reflects the incident laser light R in a direction orthogonal to the scanning direction (X direction) of the first scanning element 13. By scanning the first scanning element 13 in a direction perpendicular to the reflecting direction of the laser light R on the first reflecting surface 15b, the optical system 1 can be downsized.

As described above, the embodiments have been described as examples of the technique in the present disclosure. For this purpose, the accompanying drawings and the detailed description have been provided. Therefore, the components described in the accompanying drawings and the detailed description may include not only components essential for solving the problem but also components that are not essential for solving the problem in order to illustrate the above technique. Therefore, it should not be immediately recognized that these non-essential components are essential based on the fact that these non-essential components are described in the accompanying drawings and the detailed description.

In addition, since the above-described embodiments are intended to illustrate the technique in the present disclosure, various changes, replacements, additions, omissions, and the like can be made within the scope of the claims or equivalents thereof.

Outline of Embodiments (1) An optical system according to the present disclosure includes a prism having an incident surface, an exit surface, and one or more reflecting surfaces, a first scanning element that scans an incident light in a first direction and reflects the light in a direction of the incident surface of the prism, and a second scanning element that scans the light exiting from the exit surface of the prism in a second direction orthogonal to the first direction. The incident surface of the prism has a convex shape with respect to the first scanning element.

As described above, when the light scanned in the first direction by the first scanning element is made incident on the incident surface of the prism, the light scanned and diffused is refracted so as to be closer to parallel by the incident surface. As a result, spreading of the optical path of the light traveling in the prism is suppressed. Thus, the prism can be downsized.

(2) In the optical system according to (1), the incident surface of the prism is a rotationally asymmetric surface having a convex shape with respect to the first direction in which the first scanning element scans.

(3) In (1) or (2), the incident surface of the prism has a smaller refractive power in a non-scanning direction than in the first direction in which the first scanning element scans.

(4) In the optical systems according to any one of (1) to (3), a first intermediate imaging position of a light flux of the light in the first direction is located in an optical path between the first scanning element and the second scanning element.

(5) In the optical system according to any one of (1) to (3), a first intermediate imaging position of a light flux of the light in the first direction is located inside the prism.

(6) In the optical system according to (4) or (5), the first intermediate imaging position is different from a second intermediate imaging position of the light flux of the light in the second direction orthogonal to the first direction. As described above, in the prism, since the first intermediate imaging position of the light flux in the first direction is not located at the second intermediate imaging position of the light flux in the second direction, even when there is a scratch or dust in a part of the first intermediate imaging position of the light flux in the first direction in the prism, an influence on the light flux in the first direction can be reduced.

(7) In the optical system according to (4) or (5), an intermediate image is not formed with respect to the light flux of the light in the second direction orthogonal to the first direction. As described above, in the prism, since the intermediate imaging position of the light flux in the first direction is not located at the intermediate imaging position of the light flux in the second direction, even when there is a scratch or dust in a part of the intermediate imaging position of the light flux in the first direction in the prism, an influence on the light flux in the first direction can be reduced.

(8) In the optical system according to any one of (1) to (7), the exit surface of the prism has a convex shape with respect to the second scanning element.

(9) In the optical system according to (8), the exit surface of the prism is a rotationally asymmetric surface having the convex shape with respect to the second direction in which the second scanning element scans.

(10) In the optical system according to (8) or (9), the exit surface of the prism has smaller refractive power in the non-scanning direction than in the second direction in which the second scanning element scans.

(11) In the optical system according to any one of (1) to (10) includes a laser element that emits a laser light as the light to the first scanning element.

(12) In the optical system according to (11), the laser element emits the laser light having a plurality of wavelengths. As described above, even when the laser element emits the laser light having the plurality of wavelengths, the incident laser light forms an intermediate image in the prism, so that chromatic aberration due to a difference in wavelengths can be reduced.

(13) In the optical system according to (12) includes a controller that controls the laser element to shift a light emission timing of the light of each wavelength for each wavelength in synchronization with scanning by the first scanning element and the second scanning element. As a result, it is possible to correct deviation of an image projected on the projection surface, due to chromatic aberration, by the light scanned by the second scanning element.

(14) Further, an optical system according to the present disclosure includes a prism having an incident surface, an exit surface, and one or more reflecting surfaces, a first scanning element that scans an incident light in a first direction and reflects the light in a direction of the incident surface of the prism, and a second scanning element that scans the light exiting from the exit surface of the prism in a second direction orthogonal to the first direction. The exit surface of the prism has a convex shape with respect to the second scanning element.

As described above, when the light exits from the exit surface of the prism to the second scanning element that scans the light in the second direction, the light exits from the prism so as to be converged on the second scanning element in a state close to parallel to the exit surface. Thus, the prism can be downsized.

(15) In the optical system according to (14), the exit surface of the prism is a rotationally asymmetric surface having the convex shape with respect to the second direction in which the second scanning element scans.

(16) In the optical system according to (14) or (15), the exit surface of the prism has a smaller refractive power in a non-scanning direction than in the second direction in which the second scanning element scans.

(17) In the optical systems according to any one of (14) to (16), a first intermediate imaging position of a light flux of the light in the first direction is located in an optical path between the first scanning element and the second scanning element.

(18) In the optical system according to any one of (14) to (16), the first intermediate imaging position of a light flux of the light in the first direction is located inside the prism.

(19) In the optical system according to (17) or (18), the first intermediate imaging position is different from a second intermediate imaging position of the light flux of the light in the second direction orthogonal to the first direction.

(20) In the optical system according to (17) of (18), an intermediate image is not formed with respect to the light flux of the light in the second direction orthogonal to the first direction.

(21) The optical system according to any one of (14) to (20) includes a laser element that emits a laser light as the light to the first scanning element.

(22) In the optical system according to (21), the laser element emits a laser light having a plurality of wavelengths.

(23) The optical system according to (22) includes a controller that controls the laser element to shift a light emission timing of the light of each wavelength for each wavelength in synchronization with scanning by the first scanning element and the second scanning element. As a result, it is possible to correct deviation of an image projected on the projection surface, due to chromatic aberration, by the light scanned by the second scanning element.

(24) In the optical system according to (1), the prism includes a first reflecting surface that reflects a light emitted from the incident surface and a second reflecting surface that reflects the light reflected by the first reflecting surface. An optical path length L1 from the incident surface to the first reflecting surface and an optical path length L2 from the first reflecting surface to the second reflecting surface satisfy:

$$L1<L2.$$

Since the optical path length from the first reflecting surface to the second reflecting surface is longer than the optical path length from the incident surface to the first reflecting surface, the incident surface can be disposed closer to the first reflecting surface than the second reflecting surface. As a result, the first scanning element can also be arranged closer to the first reflecting surface, and the size of the entire optical system can be reduced.

(25) An optical system according to the present disclosure includes a prism having an incident surface, an exit surface, and one or more reflecting surfaces, a first scanning element that scans an incident light in a first direction and reflects the incident light in a direction of the incident surface of the prism, and a second scanning element that scans the light exiting from the exit surface of the prism in a second direction orthogonal to the first direction. The prism has a first reflecting surface that reflects the light emitted from the incident surface, and a second reflecting surface that reflects the light reflected by the first reflecting surface. An optical path length L1 from the incident surface to the first reflecting surface and an optical path length L2 from the first reflecting surface to the second reflecting surface satisfy L1<L2.

Since the optical path length from the first reflecting surface to the second reflecting surface is longer than the optical path length from the incident surface to the first reflecting surface, the incident surface can be disposed closer to the first reflecting surface than the second reflecting surface, so that the first scanning element can also be arranged closer to the first reflecting surface. As a result, the size of the entire optical system can be reduced.

(26) In the optical system according to (25), the first reflecting surface is inclined with respect to the light that enters on a plane including a scanning axis of the first scanning element and the light transmitted through the incident surface. As a result, the light can be reflected in the direction of the scanning axis of the first scanning element to downsize the prism.

The present disclosure is applicable to an optical apparatus employing a refractive optical system such as a prism.

EXPLANATIONS OF LETTERS OR NUMERALS

1 Optical system
11 Laser element
11a Pupil diameter
13 First scanning element
15 Prism
15a Incident surface
15b First reflecting surface
15c Second reflecting surface
15d Exit surface
17 Second scanning element
19 Projection surface
21 Controller

The invention claimed is:

1. An optical system comprising:
a prism having an incident surface, an exit surface, and one or more reflecting surfaces;
a first scanning element configured to scan in a first direction a light that enters and reflect the light in a direction of the incident surface of the prism; and
a second scanning element configured to scan in a second direction the light that exits from the exit surface of the prism, the second direction being orthogonal to the first direction, wherein
the incident surface of the prism, incident on the light scanned by the first scanning element, has a convex shape with respect to the first scanning element, and
a two-dimensional image is formed from the light incident on the first scanning element by scanning in the first direction by the first scanning element and scanning in the second direction by the second scanning element.

2. The optical system according to claim 1, wherein
the incident surface of the prism is a rotationally asymmetric surface having a convex shape with respect to the first direction in which the first scanning element scans.

3. The optical system according to claim 1, wherein
the incident surface of the prism has a smaller refractive power in a non-scanning direction than in the first direction in which the first scanning element scans.

4. The optical system according to claim 1, wherein
a first intermediate imaging position of a light flux of the light in the first direction is located in an optical path between the first scanning element and the second scanning element.

5. The optical system according to claim 1, wherein
a first intermediate imaging position of a light flux of the light in the first direction is located inside the prism.

6. The optical system according to claim 4, wherein
the first intermediate imaging position is different from a second intermediate imaging position of the light flux of the light in the second direction orthogonal to the first direction.

7. The optical system according to claim 4, wherein
an intermediate image is not formed with respect to the light flux of the light in the second direction orthogonal to the first direction.

8. The optical system according to claim 1, wherein
the exit surface of the prism, from which the light transmitted through the prism exits, has a convex shape with respect to the second scanning element.

9. The optical system according to claim 8, wherein
the exit surface of the prism is a rotationally asymmetric surface having the convex shape with respect to the second direction in which the second scanning element scans.

10. The optical system according to claim 8, wherein
the exit surface of the prism has a smaller refractive power in a non-scanning direction than in the second direction in which the second scanning element scans.

11. The optical system according to claim 1, comprising:
a laser element configured to emit a laser light as the light to the first scanning element.

12. The optical system according to claim 11, wherein the laser element emits the laser light having a plurality of wavelengths.

13. The optical system according to claim 12, comprising:
a controller configured to control the laser element to shift a light emission timing of the light of each wavelength for each of the plurality of wavelengths in synchronization with scanning by the first scanning element and the second scanning element.

14. The optical system according to claim 1, wherein
the prism includes a first reflecting surface that reflects the light emitted from the incident surface, and a second reflecting surface that reflects the light reflected by the first reflecting surface, and an optical path length L1 from the incident surface to the first reflecting surface and an optical path length L2 from the first reflecting surface to the second reflecting surface satisfy $L1<L2.$ 15. An optical system comprising:
a prism having an incident surface, an exit surface, and one or more reflecting surfaces;
a first scanning element configured to scan in a first direction a light that enters and reflect the light in a direction of the incident surface of the prism; and
a second scanning element configured to scan in a second direction the light that exits from the exit surface of the prism, the second direction being orthogonal to the first direction, wherein
the exit surface of the prism, from which the light transmitted through the prism exits, has a convex shape with respect to the second scanning element, and
a two-dimensional image is formed from the light incident on the first scanning element by scanning in the first direction by the first scanning element and scanning in the second direction by the second scanning element.

16. The optical system according to claim 15, wherein the exit surface of the prism is a rotationally asymmetric surface having the convex shape with respect to the second direction in which the second scanning element scans.

17. The optical system according to claim 15, wherein the exit surface of the prism has a smaller refractive power in a non-scanning direction than in the second direction in which the second scanning element scans.

18. The optical system according to claim 15, wherein a first intermediate imaging position of a light flux of the light in the first direction is located in an optical path between the first scanning element and the second scanning element.

19. The optical system according to claim 15, wherein a first intermediate imaging position of a light flux of the light in the first direction is located inside the prism.

20. The optical system according to claim 18, wherein the first intermediate imaging position is different from a second intermediate imaging position of the light flux of the light in the second direction orthogonal to the first direction.

21. The optical system according to claim 18, wherein an intermediate image is not formed with respect to the light flux of the light in the second direction orthogonal to the first direction.

22. The optical system according to claim 15, comprising: a laser element configured to emit a laser light as the light to the first scanning element.

23. The optical system according to claim 22, wherein the laser element emits the laser light having a plurality of wavelengths.

24. The optical system according to claim 23, comprising: a controller configured to control the laser element to shift a light emission timing of the light of each wavelength for each of the plurality of wavelengths in synchronization with scanning by the first scanning element and the second scanning element.

25. An optical system comprising:
a prism having an incident surface, an exit surface, and one or more reflecting surfaces;
a first scanning element configured to scan an incident light in a first direction and reflect the incident light in a direction of the incident surface of the prism; and
a second scanning element configured to scan the light exiting from the exit surface of the prism in a second direction orthogonal to the first direction, wherein
the prism includes a first reflecting surface that reflects the light emitted from the incident surface, and a second reflecting surface that reflects the light reflected by the first reflecting surface, and
since an optical path length L1 from the incident surface to the first reflecting surface and an optical path length L2 from the first reflecting surface to the second reflecting surface satisfy
L1<L2, the incident surface is disposed closer to the first reflecting surface than the second reflecting surface in a direction perpendicular to the first direction and the second direction, and
a two-dimensional image is formed from light incident on the first scanning element by scanning in the first direction by the first scanning element and scanning in the second direction by the second scanning element.

26. The optical system according to claim 25, wherein the first reflecting surface is inclined with respect to the light that enters on a plane including a scanning axis of the first scanning element and the light transmitted through the incident surface.

* * * * *